United States Patent [19]

Boudet et al.

[11] Patent Number: 5,266,711

[45] Date of Patent: Nov. 30, 1993

[54] PROCESS FOR THE PREPARATION OF 3-BENZOYL BENZOFURAN DERIVATIVES

[75] Inventors: Bernard Boudet; Jean R. Dormoy; Alain Heymés, all of Sisteron, France

[73] Assignee: Sanofi, Paris, France

[21] Appl. No.: 597,684

[22] Filed: Oct. 16, 1990

[30] Foreign Application Priority Data

Oct. 23, 1989 [FR] France ............... 89 13851

[51] Int. Cl.⁵ .................................... C07D 307/80
[52] U.S. Cl. ............................... 549/468; 549/467
[58] Field of Search ............ 549/468, 467, 488, 58; 548/530

[56] References Cited

U.S. PATENT DOCUMENTS

| | | | |
|---|---|---|---|
| 3,947,470 | 3/1976 | Brenner et al. | 549/468 |
| 3,950,355 | 4/1976 | Carson | 549/530 |
| 4,766,223 | 8/1988 | Grain et al. | 549/468 |
| 4,780,480 | 10/1988 | Dunn | 549/468 |

FOREIGN PATENT DOCUMENTS 0210156  6/1986  European Pat. Off. .

OTHER PUBLICATIONS

Chemical Abstracts, vol. 94, No. 23, Jun. 8, 1981, p. 640, résumé 192122b, Columbus, Ohio, US; and HU-A-18 236 (E. GY. T. Gyogyszervegyeszeti Gyar) May 28, 1980.

Journal of Organic Chemistry, vol. 48, No. 19, Sep. 23, 1983, pp. 3214–3219, American Chemical Society, Easton, US; M. Kakushima et al.: "Regioselective synthesis of acylpyrroles".

Primary Examiner—C. Warren Ivy
Assistant Examiner—P. G. Spivack
Attorney, Agent, or Firm—Wegner, Cantor, Mueller & Player

[57] ABSTRACT

The invention relates to a process for the preparation of 3-benzoyl benzofuran derivatives of general formula:

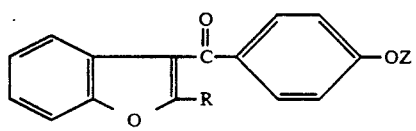

wherein a benzofuran derivative of general formula:

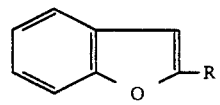

is reacted in situ in the presence of aluminium chloride successively with phosgene or oxalyl chloride, and then with a phenolic derivative of general formula:

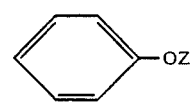

to produce a complex which is hydrolysed to form the desired compound of 3-benzoyl benzofuran.

10 Claims, No Drawings

PROCESS FOR THE PREPARATION OF 3-BENZOYL BENZOFURAN DERIVATIVES

The present invention relates in a general manner to a novel process for the preparation of benzoyl benzofuran derivatives.

More precisely, the object of the invention is a novel process for the preparation of 3-benzoyl benzofuran derivatives of general formula:

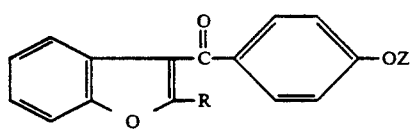

I in which

R is selected from a $C_1$–$C_8$ linear or branched alkyl radical, a $C_3$–$C_6$ cycloalkyl radical and a phenyl group substituted or not by one or several substituents, identical or different, selected from halogen atoms, for example fluorine, chlorine or bromine and $C_1$–$C_4$ alkyl, $C_1$–$C_4$ alkoxy and nitro groups, Z is selected from hydrogen or the methyl radical.

By "$C_1$–$C_8$ linear or branched alkyl radical" is meant in particular methyl, ethyl, n-propyl, isopropyl, n-butyl, isobutyl, tert.butyl, n-pentyl, neopentyl, n-hexyl, n-heptyl or n-octyl radicals.

Similarly, by "$C_3$–$C_6$ cycloalkyl radical" is meant in particular cyclopropyl or cyclohexyl radicals.

Thus, by taking into account the values given above, R may denote in particular a methyl, ethyl, n-propyl, isopropyl, n-butyl, isobutyl, tert.butyl, 1-methyl propyl, n-pentyl, neopentyl, phenyl, mono-fluoro-, mono-chloro- or mono-bromo-phenyl, difluoro-, dichloro- or dibromo-phenyl, mono-methyl- or dimethyl-phenyl, mono-methoxy- or dimethoxy-phenyl radical or a methyl-phenyl radical substituted by halogen.

By "$C_1$–$C_4$ alkyl radical", is meant more particularly a methyl, ethyl, n-propyl, isopropyl, n-butyl, isobutyl or tert.butyl radical.

By "$C_1$–$C_4$ alkoxy radical", is meant a hydroxyl group substituted by a $C_1$–$C_4$ alkyl radical as defined above.

Of the compounds of formula I, those in which R denotes an ethyl or n-butyl radical constitute preferred compounds.

The 3-benzoyl benzofuran derivatives of formula I may be widely used as intermediates in particular for the final synthesis of benzofuran derivatives described in the French patents No. 1 260 578 and 1 339 389.

Such derivatives are in particular benziodarone or 2-ethyl 3-(3,5-diiodo 4-hydroxy benzoyl) benzofuran, benzbromarone or 2-ethyl 3-(3,5-dibromo 4-hydroxy benzoyl) benzofuran and amiodarone or 2-n-butyl 3-(3,5-diiodo 4,β-diethylaminoethoxybenzoyl) benzofuran.

These compounds have been shown to be particularly valuable for their therapeutic applications.

Thus, benziodarone has been shown to be useful on account of its coronary dilating and uricosuric action, benzbromarone by its uricosuric effect and amiodarone by its antianginal and cardiac antiarrythmic properties.

Some derivatives of formula I have also been shown to be useful as therapeutic agents. For example, 2-ethyl 3-(4-hydroxy benzoyl) benzofuran or benzarone which has been shown to be efficacious on account of its phlebotonic effect and as an inhibitor of capillarovenous inflammatory reactions.

The preparation of 3-anisoyl- or 3-benzoyl-benzofuran derivatives by the Friedel-Crafts reaction is widely known in the chemical literature.

For example:

the French patent No. 1 260 578 which reports the reaction between a 2-alkyl benzofuran and anisoyl chloride in the presence of stannic chloride as catalyst and in carbon disulfide as solvent.

Anisoyl chloride may be obtained, for example, from anisic acid and thionyl chloride.

Eur. J. Med. Chem.—Chimica Therapeutica 1974, 9, No. 1, pp. 19–25 which describes the condensation of a 2-alkyl 3-chlorocarbonyl benzofuran derivative with a 3,5 dialkyl anisole in the presence of aluminum chloride as catalyst and in dichloroethane as solvent, the 3-chlorocarbonyl derivative being obtained according to the following sequence of steps:

a) reaction of a 2-alkyl benzofuran with acetyl chloride in the presence of stannic chloride, b) reaction of the 2-alkyl 3-acetyl benzofuran obtained with sulfuryl bromide or chloride, c) heating of the 2-alkyl 3-haloacetyl benzofuran obtained in pyridine, d) hydrolysis of the 2-alkyl 3-ω-halopyridinium acetyl benzofuran obtained in the presence of sodium hydroxide, e) regeneration of the 2-alkyl benzofuran 2-carboxylic acid from its sodium salt thus obtained, f) reaction of the 2-alkyl benzofuran 3-carboxylic acid with thionyl chloride to generate 2-alkyl 3-chlorocarbonyl benzofuran.

Other Lewis catalysts have been described in the Friedel-Crafts reaction including, for example, ferric chloride (patent application EP-A-O 210 156) or aluminium chloride.

This latter was used in a process reported in the Hungarian patent No. 175 906 (Chem. Abstr. 94, 192122b) according to which 2-ethyl 3-(4-hydroxy benzoyl) benzofuran is prepared in the following manner:

a) the reaction of one equivalent of 2-ethyl benzofuran with one equivalent of anisoyl chloride (prepared immediately prior to use from anisic acid and thionyl chloride) is carried out in the presence of 1.02 equivalents of aluminium chloride in chlorobenzene at 0° C., b) the complex obtained is demethylated by the addition of 3.08 equivalents of aluminium chloride and heated to 70° C., c) hydrolysis at room temperature produces, after purification and separation, the desired compound in a yield of 50.5%.

In conclusion, the methods cited above all require a process making use of a single Friedel-Crafts reaction for the formation of the final ketone, the chlorocarbonyl substituent necessary for the condensation being attached either to the benzofuran derivative or to the methoxybenzene derivative from the start.

Consequently, these procedures of the prior art require the preparation of a suitable chlorocarbonyl derivative as intermediate which may, in some cases, increase considerably the total number of steps of the process and, in consequence, the cost price of the final product.

The research into a relatively cheap industrial process making use of readily accessible synthetic intermediates as well as a limited number of steps and giving a satisfactory yield of final product consequently remains of unquestionable importance.

Moreover, it is known that the Friedel-Crafts reaction may also be accomplished by reaction of phosgene or oxalyl chloride on the aromatic substrate Ar.

In this case, the symmetrical ketone Ar—Co—Ar is obtained as major product accompanied by a very small amount of acid $ArCO_2H$ according to the scheme:

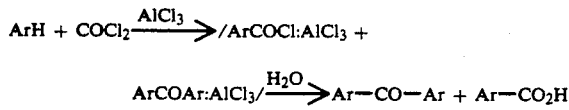

The only method for obtaining the acid in a good yield consists of using carbon disulfide as solvent since the /ArCOCl:AlCl$_3$/ complex is not soluble, precipitates and thus cannot react with a second molecule of ArH to give the symmetrical ketone.

The formation of symmetrical ketones in this type of reaction consequently limits the scope of a process for the preparation of ketones by a double Friedel-Crafts reaction between two different aromatic compounds and phosgene.

In the present state of knowledge, no example exists of the preparation of asymmetric aromatic ketones based on this type of process.

It has now been found according to the invention that it is possible to obtain asymmetric aromatic ketones, in this case the 3-benzoyl benzofuran derivatives of formula I, by double Friedel-Crafts reaction using phosgene and two different aromatic compounds.

Thus, according to the invention, the compounds of formula I are prepared by reacting in situ in the presence of an aluminium chloride as catalyst at a temperature between −25° C. and room temperature and in an apolar aprotic solvent, a benzofuran derivative of general formula:

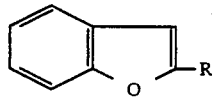

in which R is as defined above, first with phosgene or oxalyl chloride, then with a phenolic derivative of general formula:

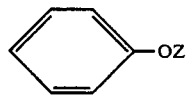

in which Z is as defined previously, in order to produce a complex which is hydrolysed to form the desired compound of formula I.

It has been observed that the relative proportions of the various reagents participating play a not inconsiderable role in the formation of side products represented by symmetric ketones.

The most suitable molar ratios used in the process of the invention with a view to promoting the production of asymmetric ketones have been found to be the following:

compound of formula II or III/phosgene or oxalyl chloride/aluminium chloride: 1/2 to 4/1 to 1.5 with a preference for the ratio 1/3/1.5, the compounds of formula II and III being in stoichiometric amounts.

The apolar aprotic solvent used in the process of the invention is preferably carbon tetrachloride or a $C_1$-$C_4$ alkyl halide such as dichloromethane or dichloroethane.

As for the hydrolysis, this is conducted at a temperature between room temperature and 50° C., and preferably at room temperature.

The process of the invention may be implemented by loading the benzofuran derivative of formula II, phosgene, the catalyst and the solvent selected into a reactor at a temperature of about −20° C. and by then carrying out the reaction at room temperature for several hours, for example from 20 to 24 hours.

The derivative of formula III is then introduced into the reaction mixture at a temperature of about −20° C., the mixture is then reheated in order to carry out the reaction at room temperature for 2 to 3 hours and the reaction medium is poured into water in order to effect the hydrolysis of the complex.

The 3-benzoyl benzofuran derivative of formula I thus obtained may then be separated in a conventional manner.

The process of the invention thus described makes it possible to produce the 3-benzoyl benzofuran derivatives of formula I with ease and in excellent yields. For example, 2-n-butyl 3-(4-methoxy benzoyl) benzofuran may be produced in yields higher than 75% according to the invention.

Furthermore, compared with the processes of the prior art, the process of the invention offers the unquestionable advantage of avoiding the preparation immediately prior to use of a chlorocarbonyl derivative and thus of reducing the number of steps considerably.

It is also possible to prepare a derivative of formula I in which Z represents hydrogen starting from the 3-(4-methoxy benzoyl) benzofuran derivative of formula I which is demethylated to the 3-(4-hydroxy benzoyl) benzofuran derivative, for example, by use of the method described in the patent EP-A-0 210 156, i.e. by reaction of aluminium chloride as demethylating reagent at the reflux temperature of the reaction mixture.

The 3-benzoyl benzofuran derivatives of formula I in which Z denotes hydrogen may also be prepared from a compound of formula II in which Z denotes the methyl group, followed by in situ demethylation of the complex formed by means of aluminium chloride, the reaction mixture being at reflux temperature.

Thus, according to this variant of the process, a benzofuran derivative of formula II is reacted in situ in the presence of aluminium chloride as catalyst at a temperature between −25° C. and room temperature and in an apolar aprotic solvent first with phosgene or oxalyl chloride, then with anisole in order to produce a complex which is demethylated in situ at the reflux temperature of the medium and in the presence of aluminium chloride, then hydrolysis is carried out in order to produce the 3-benzoyl benzofuran derivatives of formula I in which Z denotes hydrogen.

The amount of aluminium chloride necessary for the Friedel-Crafts reactions is as previously indicated from 1 to 1.5 equivalents per equivalent of compound of formula II whereas the amount of aluminium chloride necessary for the demethylation is one equivalent per equivalent of compound of formula II.

This variant of the process offers, in particular, the advantage of being able to carry out all of the reactions necessary for the production of the 3-(4-hydroxy benzoyl) benzofuran derivatives of formula I in a single reaction mixture, without isolation of any intermediate.

Furthermore, since aluminium chloride is used both for the Friedel-Crafts reactions and for demethylation, it is possible to reduce very appreciably the amount of this reagent compared with the quantities recommended in the Hungarian patent No. 175.906 which makes provision for the use of a total of 4 equivalents of aluminium chloride.

The variant of the process thus described makes it possible to prepare the 3-(4-hydroxy benzoyl) benzofuran derivatives of formula I in very high yields. In the case in particular of the preparation of 2-n-butyl 3-(4-hydroxy benzoyl) benzofuran, it has been possible to obtain yields of at least 70% by applying this variant of the process.

As mentioned previously, the derivatives of 3-benzoyl benzofuran of formula I can be used for the preparation of benziodarone, benzbromarone or amiodarone.

For example, benziodarone and benzbromarone may be prepared, in particular, by iodination or bromination, respectively, of 2-ethyl 3-(4-hydroxy benzoyl) benzofuran in homogeneous solution and in the presence of an alkali metal acetate buffer/acetic acid solution and amiodarone may be obtained by iodination of 2-n-butyl 3-(4-hydroxy benzoyl) benzofuran, in a manner analogous to that prescribed previously to produce 2-n-butyl 3-(3,5-diiodo-4-hydroxy benzoyl) benzofuran, followed by an etherification by means of 1-diethylamino 2-chloro ethane hydrochloride in the presence of an alkali metal carbonate/alkali metal bicarbonate buffer solution.

The following examples illustrate the invention and the preparation of amiodarone.

EXAMPLE 1

Preparation of 2-n-butyl 3-(4-methoxy benzoyl) benzofuran 40 ml of anhydrous dichloroethane are placed in a reactor under argon and cooled to −20° C. Then 3 ml (41.87 mmoles) of phosgene, 2.5 ml (14.2 mmoles) of 2-n-butyl benzofuran and 2.13 g (15.96 mmoles) of aluminium chloride are successively introduced into the reactor. The solution is gradually heated to room temperature, stirred during 24 hours and cooled to −20° C.

1.55 ml (14.25 mmoles) of anisole are added and the solution is then heated to room temperature, stirred for 2 hours and poured into 100 ml of water. After 30 mn of vigorous stirring, the organic phase is separated, washed with 30 ml of a saturated solution of sodium bicarbonate, 40 ml of water then dried over sodium sulfate.

After evaporation of the solvent and purification of the crude product obtained on a column of silica (eluant: methylene chloride/hexane 1/1), 3.44 g (11.17 mmoles) of 2-n-butyl 3-(4-methoxy benzoyl) benzofuran are obtained.

Yield: 78.7%.

EXAMPLE 2

Preparation of 2-n-butyl 3-(4-hydroxy benzoyl) benzofuran 40 ml of anhydrous dichloroethane are placed in a dry round bottomed flask under argon and cooled to −20° C. 3 ml (41.87 mmoles) of phosgene, 2.5 ml (14.2 mmoles) of 2-n-butyl benzofuran and 2.13 g (15.96 mmoles) of aluminium chloride are successively introduced into the flask.

The solution is heated to room temperature, stirred for 24 hours and cooled to −20° C. 1.55 ml (14.25 mmoles) of anisole are then added and the solution is then reheated to 25° C.

Stirring is maintained for 2 hours and 1.9 g (14.23 mmoles) of aluminium chloride are added. The mixture is heated at reflux for 8 hours. After being cooled to about 40° C., the reaction mixture is poured into 100 ml of water and stirred for 30 mn. The organic phase is then separated, washed with 30 ml of a saturated solution of sodium bicarbonate, then with 40 ml of water. It is dried over sodium sulfate and decolorized. After evaporation of the solvent and purification of the crude product obtained on a column of silica (eluant: methylene chloride), 2.9 g (9.87 mmoles) of 2-n-butyl 3-(4-hydroxy benzoyl) benzofuran are obtained.

Yield: 70%

M.p.: 120° C.

EXAMPLE 3

Preparation of 2-n-butyl 3-(3,5-diiodo 4-β-diethylamino ethoxy benzoyl) benzofuran hydrochloride a) 2-n-butyl 3-(4-hydroxy benzoyl) benzofuran To a solution of 2 g (6.5 mmoles) of 2-n-butyl 3-(4-methoxy benzoyl) benzofuran in 30 ml of dichloroethane 1.82 g (13.6 mmoles) of aluminium chloride are added under argon. The mixture is heated at reflux for 9 hours, then cooled to room temperature. The reaction mixture is then poured into 50 ml of water, stirred vigorously for 30 minutes, then the organic phase is separated. It is washed 3 times with 30 ml of water, dried over sodium sulfate and decolorized by means of diatomaceous earth. After evaporation of the solvent, 1.9 g (6.5 mmoles) of 2-n-butyl 3-(4-hydroxy benzoyl) benzofuran are obtained.

Yield: 100%

M.p.: 119°–120° C.

b) 2-n-butyl 3-(3,5-diiodo 4-hydroxy benzoyl) benzofuran 540 g of methanol are introduced into a 4 l reactor. 300 g (2.4 moles) of sodium acetate trihydrate, 286 g of iodine and 424 g of moist recovered iodine (a total of 2.3 moles) are successively added with stirring. The reaction mixture is brought to 30° to 35° C. and 294 g (1 mole) of 2-n-butyl 3-(4-hydroxy benzoyl) benzofuran are introduced in one portion.

It is rinsed in with 60 g of methanol and the mixture is heated at reflux for 30 to 45 mn (temperature in the mass: 70° to 74° C.). Heating is stopped and a solution prepared beforehand from 90 g (2.2 moles) of sodium hydroxide pellets in 400 g of purified water is introduced during about 10 mn. The exothermic nature of the reaction maintains reflux (76°/77° C. in the mass) during the period of the addition. The mixture is maintained at reflux for 2 h, then the apparatus is converted into an apparatus for distillation at atmospheric pressure. An aqueous solution of 320 g of sodium bisulfite (35° Bé) is added within about 20 mn and the distillation is continued until the temperature in the mass reached 97° to 100° C. (distillation head temperature: 87° C.). Thus, about 800 ml (about 680 g) of solvent are distilled. Cooling to 75° to 80° C. is performed by means of a waterbath and 200 g of purified water, 215 g of 36% of hydrochloric acid and 1600 g of toluene are added successively and in that order. The mixture is heated at reflux for 10 mn (temperature of the mass: 84° C.—evolution of sulfur dioxide) and the lower aqueous phase is decanted. The toluene layer is washed at 75° to 80° C. successively with 400 g of purified water, 100 g of an aqueous solution of sodium bisulfite and with each of 2 portions of 400 g of purified water. The maximum amount of aqueous phase is decanted after the last washing and the residue is treated with 22 g of active charcoal for 30 mn at reflux. The mixture is filtered hot, rinsed with 380 g of hot toluene and the filtrates are pooled.

A toluene solution of 2-n-butyl 3-(3,5-diiodo 4-hydroxy benzoyl) benzofuran is thus obtained which is used as such.

In a manner similar to that just described but starting from 266.3 g (1 mole) of 2-ethyl 3-(4-hydroxy benzoyl) benzofuran, 2-ethyl 3-(3,5-diiodo 4-hydroxy benzoyl) benzofuran or benziodarone is obtained after removal of the toluene by distillation.

Similarly, starting from 266.3 g (1 mole) of 2-ethyl 3-(4-hydroxy benzoyl) benzofuran and bromine, 2-ethyl 3-(3,5-dibromo 4-hydroxy benzoyl) benzofuran or benzbromarone is obtained after removal of the toluene by distillation.

c) 2-n-butyl 3-(3,5-diiodo 4-β-diethylaminoethoxy benzoyl) benzofuran

The toluene solution of 2-n-butyl 3-(3,5-diiodo 4-hydroxy benzoyl) benzofuran obtained in paragraph b) is introduced into a reactor together with 800 g of purified water and 177.3 g (1.03 mole) of 1-diethylamino 2-chloroethane hydrochloride. The reaction mixture is brought to 40°±2° C. with stirring and maintained there for 15 mn. By controlling the evolution of carbon dioxide, 416 g (3 moles) of anhydrous potassium carbonate are then added in a slow stream. The temperature is gradually raised to reflux within 1 h. The mixture is maintained at this temperature for 3 h, the aqueous saline layer is decanted at 75°±5° C. and the toluene layer is washed at this temperature with each of 4 portions of 800 g of purified water. The toluene solution is treated at 60° C. with 20.5 g of active charcoal, filtered, rinsed with about 220 g of toluene and the filtrates are pooled.

A toluene solution of 2-n-butyl 3-(3,5-diiodo 4-β-diethylaminoethoxy benzoyl) benzofuran are thus obtained in the form of the free base or amiodarone.

d) 2-n-butyl 3-(3,5-diiodo 4-β-diethylaminoethoxy benzoyl) benzofuran hydrochloride The solution of 2-n-butyl 3-(3,5-diiodo 4-β-diethylaminoethoxy benzoyl) benzofuran obtained in paragraph c) is brought to 60° C. and 38.5 g of hydrogen chloride are introduced by means of a descending inlet tube. The temperature of the mass is allowed to rise as a consequence of the exothermic nature of the reaction without, however, exceeding 75° C.

The pH is verified to be quite acid at the end of the introduction and after 30 mn of contact at 70°±5° C.

The mixture is gradually placed under water pump vacuum and about 400 ml of toluene/water/hydrochloric acid are distilled (end of distillation: residual pressure ≦150 mm; temperature of the mass ≦75° C. Crystallization is induced with a waterbath and gentle stirring during about 8 hours and the crystals are filtered off at 10° to 15° C. They are rinsed with each of 4 portions of 180 ml of filtered toluene and dried in a ventilated oven at 60° C. to constant weight.

About 647.5 g of 2-n-butyl 3-(3,5-diiodo 4-β-diethylamino ethoxy benzoyl) benzofuran hydrochloride or amiodarone hydrochloride are thus obtained.

Yield: about 95% (with respect to 2-n-butyl 3-(4-hydroxy benzoyl) benzofuran).

We claim:

1. A process comprising reacting a benzofuran of the formula:

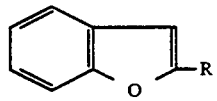

II in which R is a $C_1$–$C_8$ linear or branched alkyl, a $C_3$–$C_6$ cycloalkyl or a phenyl group optionally substituted with one or several substituents, identical or different, selected from the group consisting of halogen atoms, $C_1$–$C_4$ alkyl, $C_1$–$C_4$ alkoxy and nitro groups, successively in situ, in the presence of an aluminum chloride catalyst at a temperature between $-25°$ C. and room temperature and in an apolar aprotic solvent, first with phosgene, then with a phenolic compound of formula:

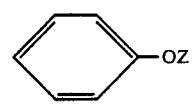

III in which Z is hydrogen or methyl, in order to produce a complex.

2. A process according to claim 1 wherein the benzofuran compound of formula II is successively:
reacted in situ, in the presence of aluminium chloride as a catalyst at a temperature between $-25°$ C. and room temperature and in an apolar aprotic solvent, first with phosgene, then with anisole, in order to produce the complex which is demethylated in situ at the reflux temperature of the medium in the presence of aluminium chloride.

3. The process of claim 2 further comprising hydrolyzing the demethylated complex in order to form a 3-benzoyl benzofuran compound of the formula:

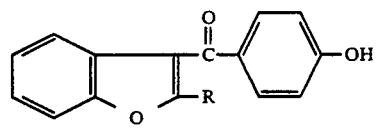

I in which R is as previously defined.

4. The process of claim 1 further comprising hydrolyzing the complex to form a 3-benzoyl benzofuran compound of the formula:

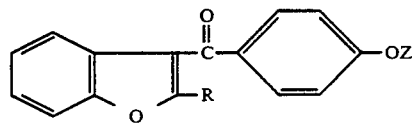

I in which R and Z are as previously defined.

5. A process according to claim 3, wherein the amount of aluminium chloride as catalyst is 1 to 1.5 equivalents per equivalent of benzofuran compound of formula II and the amount of aluminium chloride necessary for the demethylation is one equivalent per equivalent of benzofuran compound of formula II.

6. A process according to claim 4, wherein the molar ratios: benzofuran derivative/phenolic derivative/phosgene aluminium chloride are 1/1/2 to 4/1 to 1.5.

7. A process according to claim 4, wherein the apolar aprotic solvent is carbon tetrachloride or a $C_1$–$C_4$ alkyl halide.

8. A process according to claim 4, wherein the hydrolysis takes place at a temperature between room temperature and 50° C.

9. A process according to claim 4, wherein R represents ethyl.

10. A process according to claim 4, wherein R represents n-butyl.

* * * * *